United States Patent [19]

Andersson

[11] Patent Number: 4,721,821
[45] Date of Patent: Jan. 26, 1988

[54] METHOD FOR PREPARING NITROBIBENZYL SYSTEMS

[75] Inventor: Sven G. B. Andersson, Malmö, Sweden

[73] Assignee: Chemical Dynamics Development AB, Skara, Sweden

[21] Appl. No.: 899,293

[22] PCT Filed: Dec. 19, 1985

[86] PCT No.: PCT/SE85/00533

§ 371 Date: Aug. 14, 1986

§ 102(e) Date: Aug. 14, 1986

[87] PCT Pub. No.: WO86/03743

PCT Pub. Date: Jul. 3, 1986

[30] Foreign Application Priority Data

Dec. 20, 1984 [SE] Sweden ............................... 8406497

[51] Int. Cl.$^4$ ............................................. C07C 79/10
[52] U.S. Cl. ...................................... 568/931; 568/928
[58] Field of Search ............................. 568/931, 928

[56] References Cited

U.S. PATENT DOCUMENTS

| | | | |
|---|---|---|---|
| 2,596,108 | 5/1952 | Treves | 568/931 X |
| 2,965,681 | 12/1960 | Stansbury, Jr. et al. | 568/931 |
| 3,006,972 | 10/1961 | Fields et al. | 568/931 X |
| 3,716,590 | 2/1973 | Caraclacu et al. | 568/931 |
| 3,895,055 | 1/1975 | Itatani et al. | 568/931 X |
| 3,950,434 | 4/1976 | Kominami et al. | 568/931 X |

FOREIGN PATENT DOCUMENTS 2161286 7/1976 France.

OTHER PUBLICATIONS

Journal of the American Chemical Society, vol. 70, No. 2, Mar. 1948 (Caston), G. R. Treves, "Investigation of the Oxidative Condensation of 2-Methoxy-4-nitrotoulene, the Use of Oxidative Catalysts", pp. 875-876.

Primary Examiner—John F. Terapane
Assistant Examiner—Susan Wolffe
Attorney, Agent, or Firm—Dennison, Meserole, Pollack & Scheiner

[57] ABSTRACT

Method for preparing bibenzyl systems with nitro groups as substituents. Toluene derivates with nitro groups are coupled oxidatively in methanolic alkali solution under influence of metal catalysts. The oxidation is preferably done with air. As catalysts metal acetonylacetonates are used. The metal can be Ni, Cu, Co, Mn, Cr or Ti. This catalyst can be used together with a crown ether. Another suitable catalyst is a metal tetraphenylporphin of porfyrin type where the metal can be Ni, vanadium (V=O) or Fe(FeIII).

12 Claims, No Drawings

METHOD FOR PREPARING NITROBIBENZYL SYSTEMS

BACKGROUND OF THE INVENTION

The invention relates to a method for synthesis of bibenzyl systems with nitro groups as substituents. Such compounds are important intermediates for pharmaceuticals.

According to the method toluene derivates with nitro groups, preferably in o- or p-position, are coupled oxidatively with air (oxygen) in methanolic KOH-solution under influence of small amounts of metal catalysts.

Several methods for the synthesis of nitrobibenzyl systems are known:

1

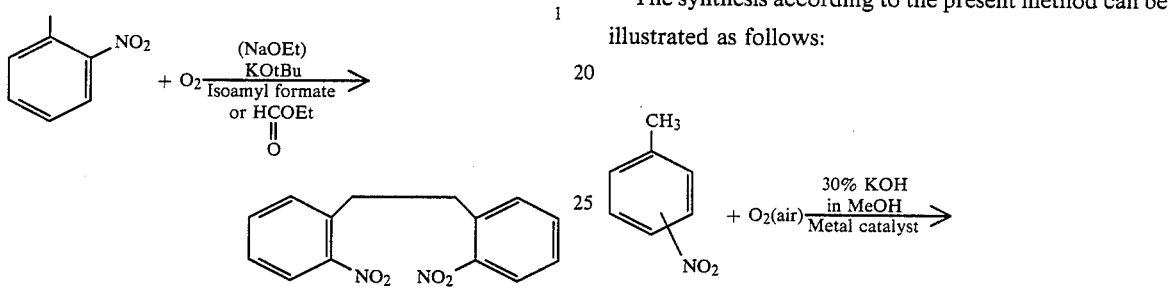

This method needs handling of KOtBu or NaOEt. The best yield, about 70%, was reached by bubbling oxygen through the reaction mixture. The recovery of the product needs handling of ether and without equivalent amount of iso amyl formiate the yield will come down to 40%. Using NaOMe about 55% is obtained. KOtBu must be used in ether. The reaction time is long, about 24 hours at 0° C.

2

Pure oxygen must be used. The yield is low, about 30%. Ethylene diamine is a catalyst.

3

Yields 51–60%. The reaction time is short but large amounts of liquid ammonia must be used. NaNH$_2$ is prepared in situ from NH$_2$. It is a drawback that sodium must be handled.

The earlier methods have several drawbacks as in certain cases bad yields, handling of chemicals with risks for the environment and comparatively expensive raw materials.

SUMMARY OF THE INVENTION

In the method according to the present invention more inexpensive raw materials are used, air is used instead of oxygen and the catalysts are only used in small amounts. The method is superior to earlier methods as to economy as well as to safety.

The synthesis according to the present method can be illustrated as follows:

Examples: o-Nitrotoluene, p-nitrotoluene.

As metal catalysts metal acetonylacetonate, Me(AcAc)$_2$, metal acetonylacetonate+crown ether, metal salt+crown ether or metal-tetraphenylporphin (porphyrin type) are used.

Metal-acetonyl-acetonate

Dibenz-1B-Crown-6-(crown ether)
2,3,11,12-dibenzo-1,4,7,10,13,16-hexaoxacyclooctadeca-2,11-diene

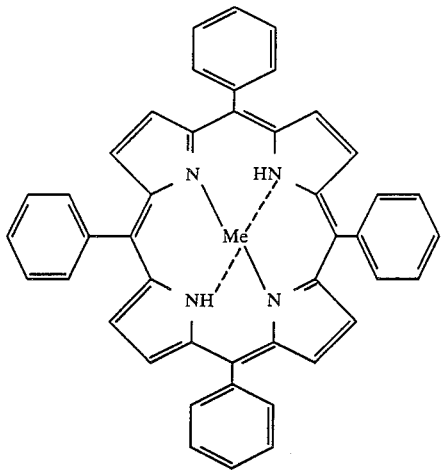

Me(porphin) = metal-tetra-phenylporphin

In the method inexpensive starting materials, suitable for full-scale production, as o-nitrotoluene, KOH, air and catalytic amounts of metal complex are used. Handling of Na or NaOEt in technical scale is avoided as well as the handling of $NaNH_2$. Oxygen is replaced by air (but it is possible to use oxygen).

The method will be further illustrated by the following non-limiting examples.

DESCRIPTION OF THE PREFERRED EMBODIMENTS

Example 1

Preparation of 2,2'-dinitrobibenzyl

A catalytic amount of a metal catalyst (0.01 g metal porfin or 0.005 g metal $(AcAc)_2 + 0.01$ g crown-ether) was added to a 33% methanolic KOH-solution, (34 g KOH in 100 ml methanol). The reaction mixture was cooled to 25° C., 2-nitrotoluene (13.7 g, 0.1 mol) was added and air was passed through the reaction mixture, the temperature of the reaction mixture being kept at 25° C. After 12 hours the passsing through of air was interrupted and 150 ml water and 50 ml methanol was added. The reaction mixture was filtered. The filter layer was dissolved in boiling toluene (benzene), was filtered when hot, was cooled and was filtered again. Recrystallisation from ethanol gave a product with m.p. 120°–121° C. Yield 24–27%. As a by-product o-nitrobenzoic acid was formed.

Example 2

Preparation of 4,4'-dinitrobibenzyl from p-nitro-toluene

The preparation was analogous to the previous example. Yield 91–99%. M.p. 179°–181° C.

Example 3

Preparation of 4,4'-dichloro-2,2'-dinitrotoluene from 2-nitro-4-chloro-toluene

The preparation was analogous to example 1. The product was precipitated from toluene with petroleum ether. Yield 23%. The IR-spectrum of the product was in accordance with the data of the literature.

The following table gives a summary of the performed experiments according to the method described above. The reaction time was 12 hours in all experiments and the ratio nitrotoluene/metal catalyst was $6.10^3$.

TABLE 1

| Nitrotoluene | Catalyst | Yield % | Product |
| --- | --- | --- | --- |
| o-Nitrotoluene | $VO(AcAc)_2$ | 8 | 2,2'-Dinitrobibenzyl |
| o-Nitrotoluene | $VO(AcAc)_2$ + crown ether | 24 | 2,2'-Dinitrobibenzyl |
| o-Nitrotoluene | VO(porphin) | 26 | 2,2'-Dinitrobibenzyl |
| o-Nitrotoluene | VO(porphin) + cat. amount $H_2O_2$, (0.1 g) | 27 | 2,2'-Dinitrobibenzyl |
| o-Nitrotoluene | No catalyst | 0 | — |
| o-Nitrotoluene | $Ni(AcAc)_2$ | 0 | — |
| o-Nitrotoluene | Ni(porphin) | 13 | 2,2'-Dinitrobibenzyl |
| o-Nitrotoluene | $Cu(AcAc)_2$ + crown ether | 14 | 2,2'-Dinitrobibenzyl |
| o-Nitrotoluene | $Co(AcAc)_2$ + crown ether | 2 | 2,2'-Dinitrobibenzyl |
| o-Nitrotoluene | $Cr(AcAc)_2$ + crown ether | 12 | 2,2'-Dinitrobibenzyl |
| o-Nitrotoluene | Fe(porphin)Cl | 22 | 2,2'-Dinitrobibenzyl |
| o-Nitrotoluene | $FeCl_2$ + crown ether | 4 | 2,2'-Dinitrobibenzyl |
| o-Nitrotoluene | $TiCl_3$ + crown ether | 0 | — |
| o-Nitrotoluene | $UD(AcAc)_2$ + crown ether | 0 | — |
| p-Nitrotoluene | $VO(AcAc)_2$ | 91 | 4,4'-Dinitrobibenzyl |
| p-Nitrotoluene | No catalyst | 75[1] | 4,4'-Dinitrobibenzyl |
| p-Nitrotoluene | VO(porphin) | 99 | 4,4'-Dinitrobibenzyl |
| 4-chloro-2-nitrotoluene | VO(porphin) | 23 | 4,4'-dichloro-2,2'-dinitrobibenzyl |
| α-chloro-4-nitrotoluene | VO(porphin) | 97 | 4,4'-Dinitrotolan[2] |

[1]From literature
[2]The reaction mixture is strongly alkaline and originally formed α-dinitrobibenzyl will eliminate HCl and give 4,4'-dinitrotolan.

Also the following nitrosubstituted toluenes were tested and gave the corresponding substituted bibenzyls in varying yields:

2,6-dinitrotoluene, 2,4-dinitrotoluene, 2,4,6-trinitrotoluene, 2-chloro-2-nitrotoluene, 5-metoxi-2-nitrotoluene, 6-chloro-2-nitrotoluene, 2-chloro-4-nitrotoluene, 3-metoxi-4-nitrotoluene.

In addition to the above mentioned catalysts also the following catalysts can be used for the syntheses according to the invention:

Ce(porphin), Pd(porphin), Pt(porphin), Hg(porphin), Zn(porphin) or Ti(porphin)

Methanolic KOH-solution can be replaced by methanolic NaOH-solution but as a rule the yield is lower.

The method according to this invention can be used with toluene derivates having as substituents in the ring a nitro-group in o- or p-position. There may also be other substituents in the ring as for example Cl, $OCH_3$, $C_3$ or other alkyl-groups. Table 2 gives examples of further syntheses.

TABLE 2

| Substituted toluene | Catalyst | Yield % | Product |
| --- | --- | --- | --- |
| 2-chloro-4-nitrotoluene | VO(porphin) | 99 | 2,2'dichloro-4,4'-dinitro-dibenzyl |
| 2-chloro-4-nitrotoluene | No catalyst | 46 | 2,2'dichloro-4,4'-dinitro-dibenzyl |
| 2-chloro-6-nitrotoluene | VO(porphin) | 18 | 2,2'-dichloro-6,6'-dinitro-bibenzyl |
| 3-methoxy-4 nitrotoluene | VO(porphin) | 22 | 3,3'-dimethoxy-4,4'-dinitro-bibenzyl |
| 3-methoxy-4 nitrotoluene | Fe(porphin)Cl | 14 | 3,3'-dimethoxy-4,4'-dinitro-bibenzyl |
| 2-Methoxy-4-nitrotoluene | VO(porphin) | 45 | 2,2'-Dimethoxy-4,4'-dinitrobibenzyl |

TABLE 2-continued

| Substituted toluene | Catalyst | Yield % | Product |
|---|---|---|---|
| 2-Methoxy-4-nitrotoluene | Fe(porphin)Cl | 36 | 2,2'-Dimethoxy-4,4'-dinitrobibenzyl |
| 5-Methoxy-4-nitrotoluene | VO(porphine) | 0 | — |

What is claimed is:

1. Method for preparing bibenzyl systems, substituted with nitro groups, comprising oxidatively coupling toluene derivatives with nitro groups in methanolic KOH or NaOH solution in the presence of a catalyst selected from the group consisting of metal acetylacetonates, metal acetylacetonates and crown ether, metal salts and crown ether, and metal tetraphenylprophins.

2. Method according to claim 1, characterized in that methanolic KOH-solution is the solution.

3. Method according to claim 1, characterized in that the oxidative coupling is carried out with air.

4. Method according to claim 1, characterized in that the oxidative coupling is carried out with oxygen.

5. Method according to claim 1, characterized in that a metal acetonyl acetonate, Me(AcAc)$_n$ is used as the catalyst.

6. Method according to claim 5, characterized in that the metal in the metal acetonyl acetonate is selected from the group consisting of Ni, Cu, Co, Mn, Cr and Ti.

7. Method according to claim 1, characterized in that a metal acetonyl acetonate and a crown ether is used as the catalyst.

8. Method according to claim 1, characterized in that a metal tetraphenylprophin of prophyrin type is used as the catalyst.

9. Method according to claim 8, characterized in that the metal in the metal tetraphenylporphin is Ni.

10. Method according to claim 8, characterized in that the metal in the metal tetraphenylporphin is present as vanadium oxide (V=O).

11. Method according to claim 8, characterized in that the metal in the metal tetraphenylporphin is present as Fe(III) in (Fe(porphin)Cl).

12. Method according to claim 1, characterized in that a combination of two or more catalysts selected from the group consisting of Me(AcAc)$_n$, crown ether and metal tetraphenylporphin is used.

* * * * *